US005167231A

United States Patent [19]

Matsui

[11] Patent Number: 5,167,231

[45] Date of Patent: * Dec. 1, 1992

[54] ULTRASONIC PROBE

[75] Inventor: Yutaka Matsui, Kawasaki, Japan

[73] Assignee: Kabushiki Kaisha Toshiba, Kawasaki, Japan

[ * ] Notice: The portion of the term of this patent subsequent to Nov. 1, 2005 has been disclaimed.

[21] Appl. No.: 138,710

[22] Filed: Dec. 23, 1987

[30] Foreign Application Priority Data

Dec. 24, 1986 [JP] Japan ........ 61-306302

Dec. 26, 1986 [JP] Japan ........ 61-315375

[51] Int. Cl.[5] ........ A61B 10/00

[52] U.S. Cl. ........ 128/662.03; 310/336; 310/366

[58] Field of Search ........ 128/660; 73/625–626; 310/336, 319, 366, 368

[56] References Cited

U.S. PATENT DOCUMENTS 4,219,846 8/1980 Aupban ........ 73/626 X
4,307,613 12/1981 Fox ........ 128/660 X
4,344,159 10/1982 Bollinger ........ 73/625 X
4,470,305 9/1984 O'Donnell ........ 128/660 X
4,550,606 11/1985 Drost ........ 310/336 X
4,640,291 2/1987 t'Hoen ........ 128/660
4,671,293 6/1987 Shanlov ........ 128/660

FOREIGN PATENT DOCUMENTS 59-108539 6/1984 Japan .

OTHER PUBLICATIONS

Non-Distinction Inspection, vol. 34, No. 9, p. 666; Kojima et al; Sep. 1985.

*Primary Examiner*—Francis Jaworski
*Attorney, Agent, or Firm*—Oblon, Fisher, Spivak, McClelland & Maier

[57] ABSTRACT

An ultrasonic probe including a piezoelectric substrate divided into a plurality of substrate sections aligned in one direction, a common electrode connected to one side of all the separated substrate sections, and plural individual electrodes being applied to an opposite side of the separated substrate sections, whereby unnecessary vibration modes are suppressed and, additionally, crosstalk characteristics are improved.

6 Claims, 4 Drawing Sheets

ULTRASONIC PROBE

BACKGROUND OF THE INVENTION

1. Field of the Invention

This invention relates generally to ultrasonic probes for transmitting and receiving ultrasonic waves for ultrasonic diagnosic apparatus, and, more particularly, to ultrasonic probes having matrix arrays of transducers.

2. Description of the Prior Art

Ultrasonic diagnostic apparatus are used to obtain tomogram images through the detection of reflected waves generated by the scanning of internal organs of a subject's body. These apparatus have come rapidly into wide use due to their real time capabilities and the superior diagnostic results obtained. Mechanical scanning and electronic scanning are among the types of scanning methods. Mechanical scanning is effected by mechanical movement of ultrasonic transducers. Electronic scanning is effected by electronic switching of a matrix array of transducers and control of the delay time. Electronic scanning has become the most popular due to its real-time operation and increased resolution. Electronic scanning systems may be classified into linear scanning and sector scanning types.

Techniques to increase the resolution in the scanning direction include a receiving dynamic focusing method. The dynamic focusing method switches focal points of the ultrasonic beams according to times corresponding to the depth into the subject's body at the time the beam is received, and combines pictures near focus points with repeated transmitting and receiving for different focus points. Wide range is achieved using multi layers as the matching layer of ultrasonic transducers in the depth direction of the subject's body. As a result, an increase of resolution can be achieved.

However, an acoustic lens has been used to focus ultrasonic beams to one point in the vertical direction to the scanning plane, e.g., the slicing direction. The width of the ultrasonic beams spreads on remote sides of the focus points. Good images are obtained near the focus points of the acoustic lens and are integrated by the width of ultrasonic beams in the slicing direction. However, the image fades on remote sides of the focus points, where the width of the ultrasonic beams spreads. As a result, microscopic structures of fine blood vessels, and the like, are not shown distinctly.

Attempts have been made to increase the resolution in the slicing direction using matrix array transducers to overcome these problems. However, a matrix array of transducers required too many transducers.

In addition, unnecessary vibration modes appear in directions other than the depth direction with general matrix array transducers, and it is difficult to remove these unnecessary vibrations, if the cutting width of the transducers approaches the thickness thereof. Conventional linear type transducers are cut fine enough, and are externally electrically. If these same methods are applied to matrix array transducers, the transducers also have to be cut very fine in the slice direction. In that case, the number of transducers becomes enormous.

As a result, manufacture has been difficult and has taken a long time. Also, large loads must be connected between the transducers and the electric circuits using leads, and transducers are expensive. In the case of matrix array transducers, the above-mentioned problems may be reduced, if individual electrodes are divided into the transducers without cutting the piezoelectric substrate. However, crosstalk between transducers through the uncut piezoelectric substrate is generated and the signal to noise ratio decreases.

It is very difficult to suppress unnecessary vibration modes by the finer division of transducers in the conventional ultrasonic probes having matrix array transducers, because the number of transducers is so great. If the transducers are divided only by individual electrodes, crosstalk characteristics will be poor.

SUMMARY OF THE INVENTION

Accordingly, one object of this invention is to provide an ultrasonic probe having improved matrix array transducers in which unnecessary vibration modes are suppressed and, additionally, crosstalk characteristics are improved.

Briefly, in accordance with one aspect of this invention, an ultrasonic probe comprises a piezoelectric substrate a common electrode on one side of the piezoelectric substrate, and individual electrodes on the other side of said piezoelectric substrate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
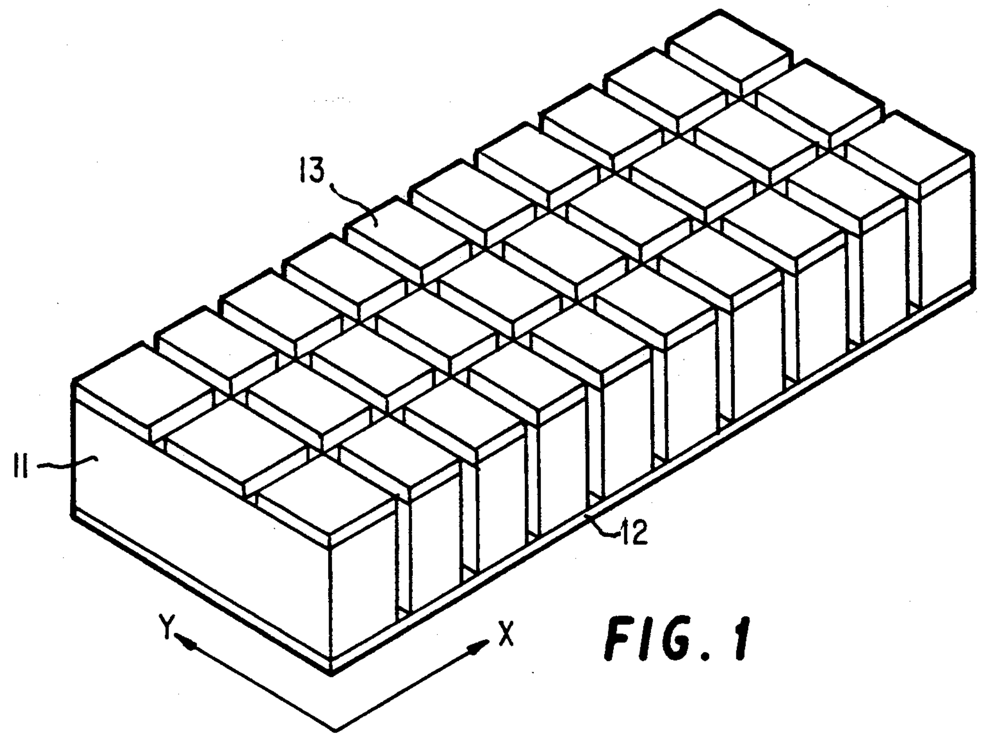
FIGS. 1 to 4 are each perspective views of different embodiments of this invention.

In FIG. 1, a piezoelectric substrate 11 made of PZT is rectangular. A common electrode 12 is formed on one side surface of the piezoelectric substrate 11 and individual electrodes 13 are formed on other side surface of the piezoelectric substrate 11.

Individual electrodes 13 are divided in the scanning direction X and the slicing direction Y, and are formed at right angles as transducers.

The piezoelectric substrate 11 is divided only in the scanning direction X having same width of individual electrodes 13. Namely, the piezoelectric substrate 11 is cut simultaneously with the cutting of the individual electrodes 13. The piezoelectric substrate 11 is not divided in the slicing direction Y. The steps of manufacturing the matrix array transducers are described below.

First, the common electrode 12 is formed on one side of the piezoelectric substrate 11 using an evaporating or sputtering processes. Belt shaped electrodes divided in the slicing direction Y are formed by a selective printing process or by photo-lithography after depositing the electrode layer on the whole surface of the other side of piezoelectric substrate 11. Next, belt shaped electrodes and piezoelectric substrate 11 are simultaneously cut at equal intervals in the scanning direction X.

A backing layer (not shown) is formed on the individual electrodes 13 and an acoustic matching layer (not shown) is formed on the common electrode 12. The acoustic layer is constructed of a single layer or multiple layers. The parameters of the acoustic layer e.g., sound speed, thickness, acoustic impedance, and the like, may be adjusted by changing the acoustic impedance between the piezoelectric substrate and the subject's body.

This ultrasonic probe can suppress unnecessary vibrations, because the cutting intervals of the piezoelectric substrate 11 are small compared to the thickness of the substrate. Unnecessary vibrations do not increase in spite of the presence of individual electrodes 13 in the Y direction, because the piezoelectric substrate 11 is not divided in the slicing direction Y. Accordingly, in this embodiment, unnecessary vibrations are suppressed and the number of divisions of individual electrodes 13 is decreased as compared to the conventional ultrasonic probe, where the piezoelectric substrate is divided in both the X and Y directions. As a result, manufacturing of the probe is easy and the yield increases. Thus, the ultrasonic probe having matrix array transducers is inexpensive to produce.

In this embodiment, the crosstalk between each elemental vibrator in the scanning direction X is decreased, because the piezoelectric substrate 11 is divided in the scanning direction X. Accordingly, the total crosstalk of the matrix array transducers is improved as compared to the conventional probe.

In the embodiment shown in FIG. 1, the number of divisions of transducers in the slicing direction Y is small, but this structure does not cause any problems.

Figure 2:
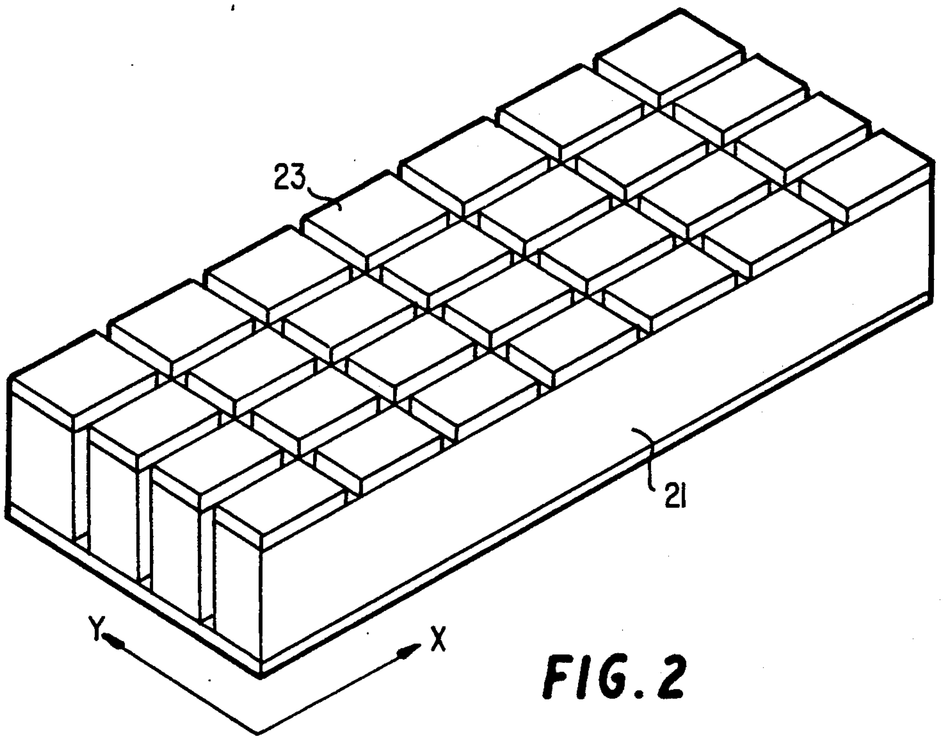

FIG. 2 shows another embodiment of this invention. Individual electrodes 23 are divided in both the X and Y directions, similar to FIG. 1. The piezoelectric substrate 21 is divided only in the slicing direction Y, inversely to FIG. 1. It is clear that this embodiment can realize similar effects with respect to the embodiment shown in FIG. 1.

Figure 3:
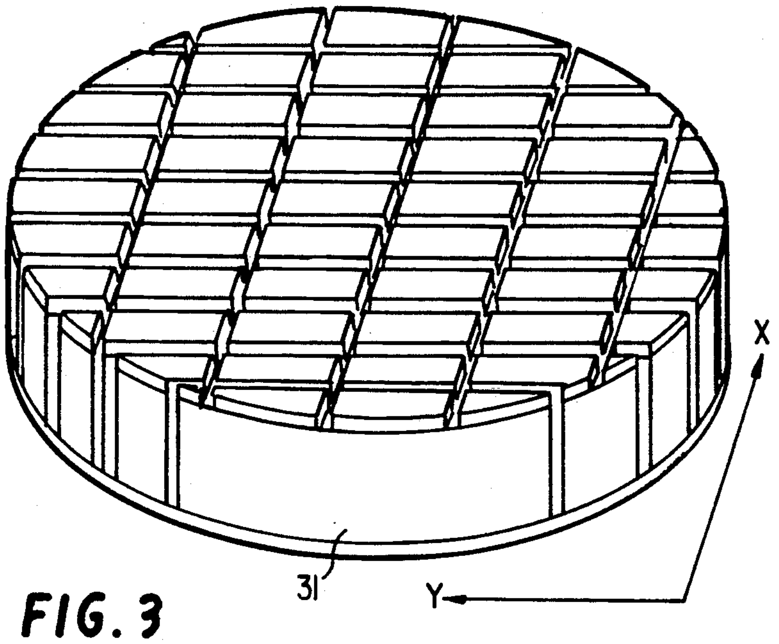

FIG. 3 shows another embodiment of this invention. The piezoelectric substrate 31 is disk shaped. Other functions and effects are similar to the above embodiments.

Figure 4:
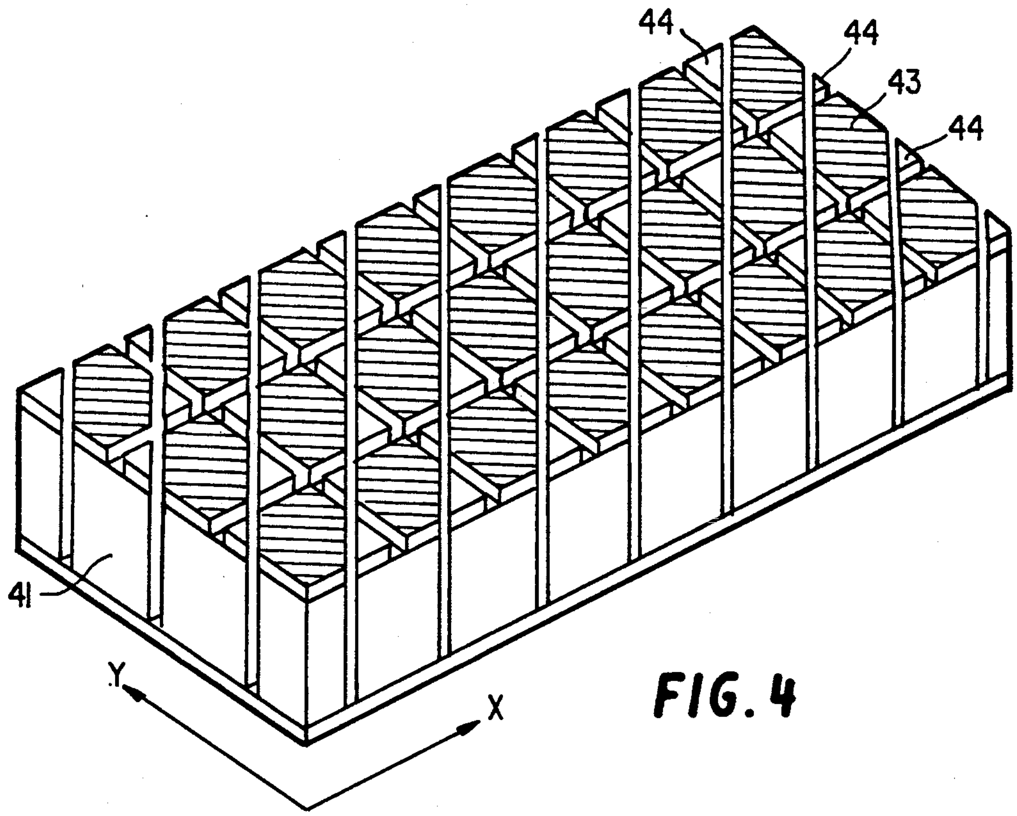

FIG. 4 shows another embodiment of this invention wherein the cutting direction of the piezoelectric substrate 41 is oblique to the scanning and slicing directions X and Y. This embodiment also has basically the same effects as the above-mentioned embodiments, particularly the decreased crosstalk in both directions, the scanning direction X and the slicing direction Y. Namely, in this structure, individual electrodes 43 are effective only at the obliquely lined portions. Piezoelectric substrate 41 is also effective only under the oblique lined portions. Therefore, each elemental vibrator is acoustically isolated by excluded portions 44 adjoining the obliquely lined portions. As a result, crosstalk is suppressed to a great extent.

Figure 5:
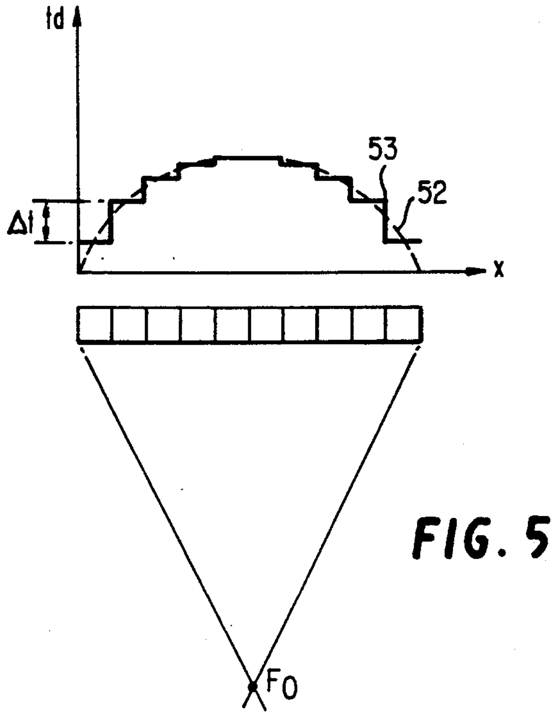
FIG. 5 is a operational diagram.

Ultrasonic beams generated by transducers are electronically focused to control the delay time of each elemental vibrator. The delay time td is quantized by the pitch of the transducers (shown in FIG. 5). Quantified delay time 53 is distributed in a step shape in the alignment direction against the ideal delay time 52 to concentrate the ultrasonic beams to some point $F_1$. In this case, differences of delay times between neighboring transducers of the matrix array 51 are desirable if the sidelobe levels near the focus point $F_0$ are within a predetermined range.

Figure 6:
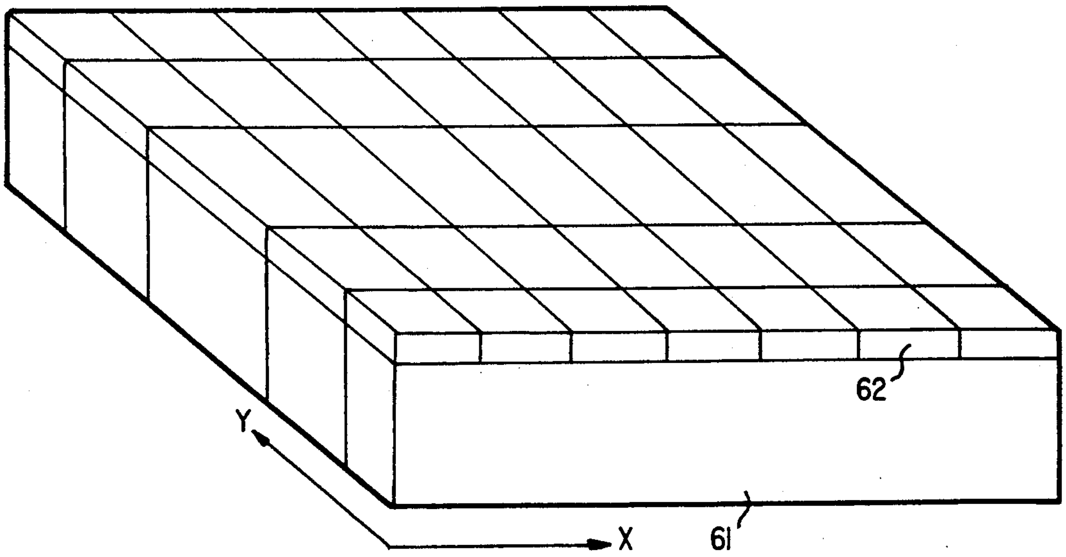
FIG. 6 is a perspective view of another embodiment of this invention.

FIG. 6 shows another embodiment of the invention. The piezoelectric substrate 61 and individual electrodes 62 are cut together in the Y direction (scanning direction) and only individual electrodes 62 are cut in the X direction (slicing direction). The widths of the individual electrodes 62 in the X direction are equal, but the widths of the cut sections of the piezoelectric substrate 61 and individual electrodes 62 are not equal. Namely, the widths of the cut sections of the piezoelectric substrate in the Y direction are narrower at the outside than at the central portion.

Figure 7:
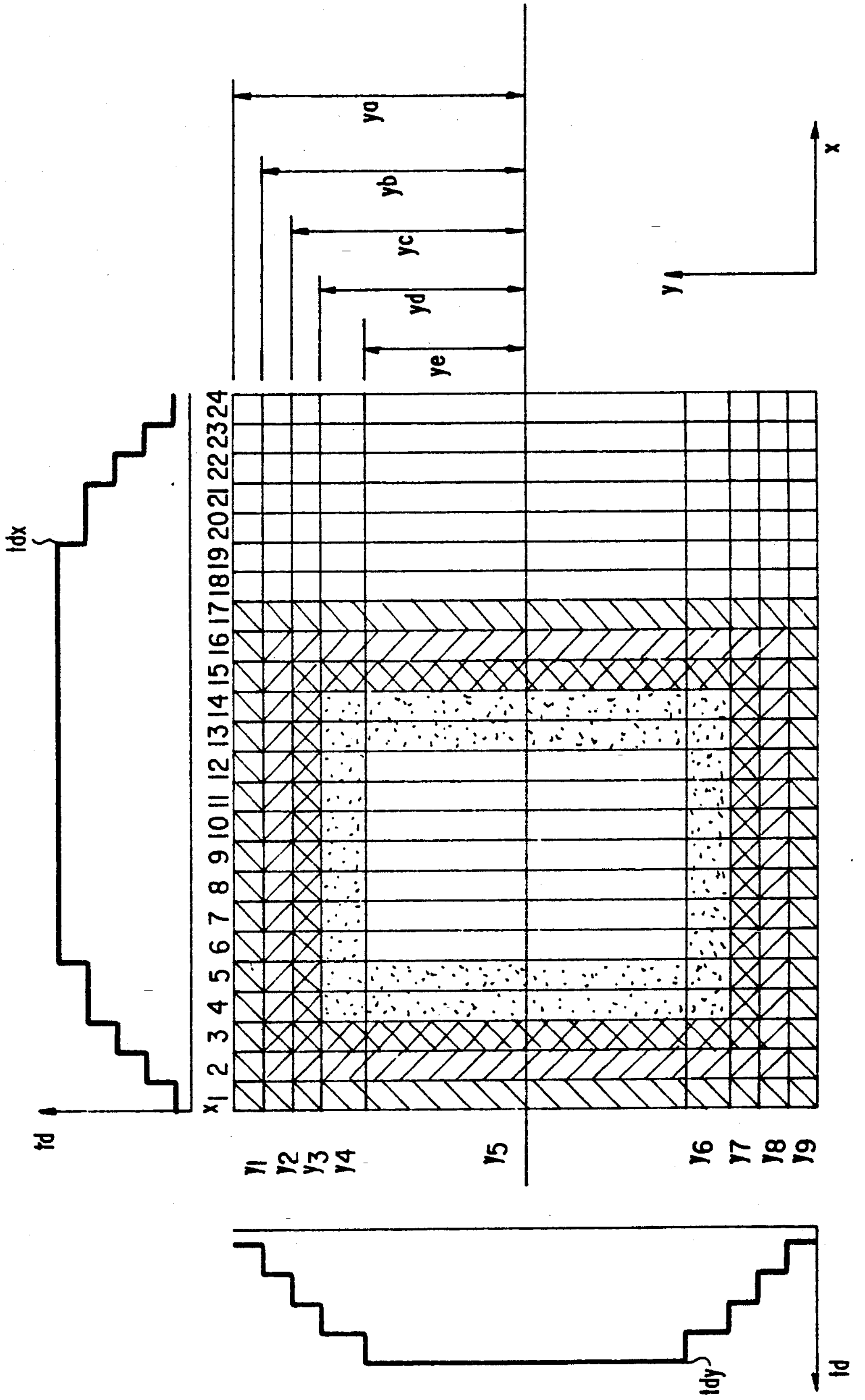
FIG. 7 is a top view of another embodiment of this invention.

FIG. 7 shows the detailed construction of another embodiment of the invention. In this embodiment, the number of electrodes in the scanning direction X is seventeen, and the number of electrodes in the slicing direction Y is nine. Linear electric scanning is operated by shifting to each successive element in the X direction. Each electrode element transmits and receives ultrasonic waves. In this case, ultrasonic beams are electrically focused by applying delay times (shown in FIG. 5) to one unit or linear plurality of elements. Matrix arrays are provided with equal widths in the scanning direction X. Therefore, correct linear electric scanning is achieved in successive steps of equal width sections. Namely, if the widths are not equal, the shifted values of ultrasonic beams generated by shifting one element are not constant. As a result, electronic focussing is also inaccurate. If the widths are constant, correct electronic scanning can be accomplished.

Delay times may be applied symmetrically from the central elemental vibrator y5 at the center of the Y direction. Transducers y1 and y9, y2 and y8, y3 and y7, and y4 and y6 are equidistant from central elemental vibrator y5. Therefore, if each pair of transducers is electrically connected, the resulting effect is electrically equivalent to five elements.

In FIG. 7, parts with the same hatching depict transducers having the same delay times. Distributions of delay times td in the scanning and slicing directions X and Y are described as $t_{dx}$ and $t_{dy}$. These $t_{dx}$ and $t_{dy}$ are quantified ideal delay time distributions arranged according to the widths of the transducers.

On the other hand, quantified errors in the delay time distribution $t_{dy}$ in the slicing direction Y are minimized by determining the length yi of transducers being at number i from the center in the alignment direction under the following conditions. The this condition, the number of the center in the slicing direction Y is set equal to n (set n=5 in this case), and the length of transducers from the center to the end is set to L.

$$
\begin{aligned}
yi &= (i \cdot L^2/n)^{\frac{1}{2}} \\
&= (i \cdot ya^2/5)^{\frac{1}{2}}
\end{aligned}
$$

However, ya=yi (i=5), yb=yi (i=4), . . . , ye=yi (i=1). This is equivalent to the Fresnel division of the matrix array in the slicing direction Y. As a result, electronic focusing with small quantified errors and suppressed sidelobes is obtained in spite of differences in the sizes of transducers.

What is claimed is:

1. An ultrasonic probe, comprising:

a piezoelectric substrate divided into a plurality of separated substrate sections aligned in one direction;

a common electrode on one side of said piezoelectric substrate electrically connected with all of the separated substrate sections;

a plurality of individual electrodes on the other side of said piezoelectric substrate, plural of said separated substrate sections being electrically connected to plural respective of the individual electrodes, wherein respective of the individual electrodes of the separated substrate sections are aligned in a different direction relative to the one direction.

2. The ultrasonic probe of claim 1 wherein the individual electrodes are rectangular.

3. The ultrasonic probe of claim 1 wherein the individual electrodes have obliquely shaped sides.

4. The probe of claim 1 wherein the substrate sections are parallel to each other.

5. The probe of claim 1 wherein the substrate sections each have a width, and the widths of the substrate sections in the one direction are unequal.

6. The probe of claim 5 wherein said substrate sections include outer sections and at least one inner section located between said outer sections the widths of the outer sections are less than the width of the at least one inner substrate section.

* * * * *

UNITED STATES PATENT AND TRADEMARK OFFICE

CERTIFICATE OF CORRECTION

PATENT NO. : 5,167,231

DATED : December 1, 1992

INVENTOR(S) : Yutaka Matsui et al.

It is certified that error appears in the above-identified patent and that said Letters Patent is hereby corrected as shown below:

On the title page, Item [75],

The inventors' information is incomplete, should be, --Yutaka Matsui, Kawasaki; Isao Uchiumi, Ohtawara; Kinya Takamizawa, Yokohama, all of Japan--

Signed and Sealed this

Twelfth Day of October, 1993

*Attest:*

BRUCE LEHMAN

*Attesting Officer*

*Commissioner of Patents and Trademarks*